(12) United States Patent
Griffith et al.

(10) Patent No.: US 6,745,077 B1
(45) Date of Patent: Jun. 1, 2004

(54) ELECTRONIC IMPEDANCE TRANSFORMER FOR INDUCTIVELY-COUPLED LOAD STABILIZATION

(75) Inventors: Glen A. Griffith, Newbury Park, CA (US); Tae W. Hahn, Northridge, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 400 days.

(21) Appl. No.: 09/975,042

(22) Filed: Oct. 9, 2001

Related U.S. Application Data

(60) Provisional application No. 60/239,288, filed on Oct. 11, 2000.

(51) Int. Cl.$^7$ ............................................. A61N 1/08
(52) U.S. Cl. .................................................... 607/61
(58) Field of Search ............................... 607/61, 62, 33, 607/57; 363/15, 16, 19

(56) References Cited

U.S. PATENT DOCUMENTS

| | | | |
|---|---|---|---|
| 3,751,605 A | 8/1973 | Michelson | 179/107 |
| 4,134,408 A | 1/1979 | Brownle et al. | 128/419 |
| 4,207,441 A | 6/1980 | Ricard et al. | 179/107 |
| 4,223,679 A | 9/1980 | Schulman et al. | 128/419 |
| 4,231,027 A | 10/1980 | Mann et al. | 340/636 |
| 4,408,608 A | 10/1983 | Daly et al. | 128/421 |
| 4,428,377 A | 1/1984 | Zollner et al. | 128/419 |
| 4,532,930 A | 8/1985 | Crosby et al. | 128/419 |
| 4,654,880 A | 3/1987 | Sontag | 455/41 |
| 5,069,210 A | 12/1991 | Jeutter et al. | 128/420.6 |
| 5,117,825 A | 6/1992 | Grevious | 128/419 |
| 5,179,511 A | 1/1993 | Troyk et al. | 363/97 |
| 5,314,453 A | 5/1994 | Jeutter | 607/61 |
| 5,466,246 A | 11/1995 | Silvian | 607/32 |
| 5,603,726 A | 2/1997 | Schulman et al. | 607/57 |
| 5,671,128 A * | 9/1997 | Nakamura et al. | 363/16 |
| 5,674,265 A | 10/1997 | Deschamps et al. | 607/60 |
| 5,690,693 A | 11/1997 | Wang et al. | 607/61 |
| 5,713,939 A | 2/1998 | Nedungadi et al. | 607/33 |
| 5,715,837 A | 2/1998 | Chen | 128/899 |
| 5,766,232 A | 6/1998 | Grevious et al. | 607/60 |
| 5,876,425 A | 3/1999 | Gord et al. | 607/56 |
| 6,067,474 A | 5/2000 | Schulman et al. | 607/57 |
| 6,073,050 A | 6/2000 | Griffith | 607/57 |
| 6,178,100 B1 * | 1/2001 | Kitano | 363/19 |
| 6,185,452 B1 | 2/2001 | Schulman et al. | 604/20 |
| 6,185,454 B1 | 2/2001 | Thompson | 604/57 |
| 6,308,101 B1 | 10/2001 | Faltys et al. | 607/57 |

FOREIGN PATENT DOCUMENTS

| | | |
|---|---|---|
| EP | 0179536 | 4/1986 |

* cited by examiner

Primary Examiner—George Manuel
(74) Attorney, Agent, or Firm—Bryant R. Gold

(57) ABSTRACT

A fixed frequency external power source having an external coil is inductively coupled with an implanted coil of an implanted medical device. The implant device has an electronic impedance transformer as part of its load circuit. Such electronic impedance transformer sets a proper voltage and current ratio (impedance) so that the coil set, i.e., the external coil and the implanted coil, are loaded with an optimal load. Such optimal loading, in turn, significantly minimizes any mismatch loss from the inductive link between the external coil and the implant coil, and allows wide ranges in the voltage and load resistance and coil separation, while at the same time maintaining an optimal load condition. The impedance transformer is especially applicable to fully implantable cochlear stimulation systems wherein, during one mode of operation, a relatively large power level must be transferred for charging the implanted power storage element, e.g., a rechargeable battery, but wherein another mode of operation, the implant is operated and powered from an external unit and a relatively small power level is transferred to the implant device. The ratio of these power levels may be large, e.g., about 30 to 1, and unless the coil set, i.e., the external coil and implanted coil, are altered between these different load conditions, a huge mismatch loss may occur, which mismatch greatly reduces the power transfer efficiency. The impedance transformer of the invention minimizes such a mismatch loss.

13 Claims, 6 Drawing Sheets

ELECTRONIC IMPEDANCE TRANSFORMER FOR INDUCTIVELY-COUPLED LOAD STABILIZATION

The present application claims the benefit of U.S. Provisional Application Serial No. 60/239,288 filed Oct. 11, 2000, which application is incorporated herein by reference.

BACKGROUND OF THE INVENTION

The present invention relates to an implantable electrical device, e.g., an implantable medical device such as an implantable cochlear stimulation system, which receives its operating power and/or which receives recharging power from an external (non-implanted) power source.

Implantable electrical devices are used for many purposes. A common type of implantable device is a tissue stimulator. A tissue stimulator includes one or more electrodes in contact with desired tissue. An electrical stimulation current is generated by the stimulator and applied to the tissue through the electrode(s).

In order for an implanted device to perform its intended function, e.g., to generate an electrical stimulation current, it needs a power source. Some implanted devices, e.g., cardiac pacemakers, employ a high capacity battery that has sufficient power stored therein to provide operating power for the device for several years. Other implanted devices, e.g., a cochlear stimulation system, do not use an implanted power source but rather receive a continuous stream of power from an external source through an rf (radio frequency) or inductive link. Yet other implanted devices include a rechargeable power source, e.g., a rechargeable battery, that must be regularly recharged, e.g., once a day, or 2–3 times per week, from an external source in order for the implanted device to operate. The present invention is intended for use with the latter two types of implanted devices, e.g., those that receive a continuous stream of operating power from an external source, and/or those that must receive power at regular intervals in order to recharge an implantable power source.

Power is typically coupled to an implanted device through inductive coupling. Inductive coupling advantageously avoids the use of wires that must pass through or penetrate the skin. With inductive coupling, an external coil receives an ac power signal. An implanted coil connected to, or forming part of, the implantable device, is placed in close proximity to the external coil so that magnetic flux generated by the ac power signal in the external coil induces an ac power signal in the second coil, much like the primary winding of a transformer couples energy to a secondary winding of the transformer, even though the two windings are not directly connected to each other. When inductively coupling power to an implanted device in this manner, an optimum power transfer condition exists only when there is a good impedance match between the implant device and the external device. While impedance matching schemes can and have been used in the external device, such matching schemes are only effective for a given distance between the external coil and the implant coil, and for a given load attached to the implant device.

Unfortunately, neither the load associated with the implant device nor the separation distance between the external coil and the implant coil are constants. Each of these parameters are, in practice, variables, that may vary, e.g., from 3-to-15 mm for the separation distance, and 20 to 300 ohms for the load. As a result, optimum power transfer between the external device and implant device is rarely achieved. Thus, a less than optimum power transfer condition exists and much of the energy sent to the external coil is lost. What is needed, therefore, is a way to assure that optimum power transfer conditions exist between the external coil and implant device at the time a power transfer is made.

For many implant devices, optimum power transfer has heretofore generally not been a serious concern inasmuch as the external device (which has generally comprised a relatively large device that is worn or carried by the patient) has been viewed as having a potentially infinite power source (through recharging and/or replacing its battery). Unfortunately, however, transferring large amounts of power without concern for how much power is lost is not only inefficient, but may create regulatory problems. That is, most regulatory agencies stipulate the power levels that may be used with an implant device.

Further, new generation external devices are being made smaller and smaller to accommodate the needs and desires of the user. For example, a behind-the-ear (BTE) external device may be used with an implantable cochlear stimulator (ICS). Such a BTE external device is about the same size as a conventional behind-the-ear hearing aid. Such smaller devices, as a practical manner, do not have a potentially infinite power source, but must be powered using a small button battery, or equivalent. Such a small battery must provide power for both the external unit and the implant unit, and achieving an efficient power transfer is a key element in assuring a long battery life.

It is known in the art, see, e.g., U.S. Pat. No. 4,654,880, to include the external coil and implant coil (as coupled to each other based on a given separation distance and load) in the oscillator circuit that sets the frequency of the signal that is coupled between the external coil and implant coil. Such circuit is somewhat self-compensating because as the transfer efficiency starts to go down (e.g., because the separation distance changes, or because the load changes) the frequency of the signal used to couple energy into the implant coil automatically changes in a direction that tends to retune the coupled coils so that the energy transfer becomes more efficient.

It is also known in the art, see, e.g., U.S. Pat. No. 5,179,511, to use a self-regulating Class E amplifier, combined with current feedback, to better control the frequency of the coupling signal so as to achieve a more optimum energy transfer.

Disadvantageously, changing the frequency of the signal coupled into the implant circuit may also create regulatory problems. That is, regulatory agencies are typically very strict about the frequencies of signals that are allowed to be transmitted, even if only transmitted over short distances.

One technique known in the art for optimally transferring power is through the use of a DC-to-DC converter. Disadvantageously, stability problems may arise when using a DC-to-DC converter. More particularly, switching regulators, a common form of DC-to-DC converters, are prone to "bistability", as discussed in the article: "Source resistance: the efficiency killer in DC-DC converter circuits", which article is attached hereto as Appendix A and is incorporated herein by reference.

In view of the above, it is evident that what is needed is a transmission scheme for use with a medical implant device that optimally transfers power to the implant device from an external device at a fixed frequency, i.e., that transfers power into the implant device from the external device with minimum power loss.

SUMMARY OF THE INVENTION

The present invention addresses the above and other needs by providing a fixed frequency external power source that is inductively coupled with an implanted device. Unlike prior art implanted devices, however, the implant device of the present invention utilizes an electronic impedance transformer as part of the load circuit in the implant device. Such electronic impedance transformer stabilizes, or makes constant, the load resistance. While the impedance seen looking into the external coil is still very much a function of the coil separation, and hence may not be optimal (this impedance follows a parabolic shaped loss curve, well known in the art, as a function of coil separation distance), it is now possible, with an adjustable stabilized load resistance (made possible by the impedance transformer of the present invention) for a smart external device to measure the impedance seen looking into the external coil (which impedance includes both the coil separation loss and the stabilized load resistance made possible by the invention) and vary the internal impedance transformer to achieve an overall better power transfer. Hence, the invention makes possible the proper voltage and current ratio (resistance) to exist, so that the coil set, i.e., the external coil and the implanted coil, are loaded with the "best available" load under the circumstances. Such best possible load, in turn, minimizes mismatch losses from the inductive link between the external coil and the implant coil, and allows wide ranges in the voltage and load resistance and coil separation, while at the same time maintains a best possible load condition.

The present invention is especially applicable to fully implantable cochlear stimulation systems. A representative fully implantable cochlear stimulation system is disclosed, e.g., in U.S. Pat. No. 6,067,474 and/or in U.S. patent application Ser. No. 09/404,966, filed Sep. 24, 1999, which patent and patent application are incorporated herein by reference. In a fully implantable system (FIS), the FIS preferably operates using power from an implanted power source, such as a rechargeable battery, which power source must be periodically recharged by transferring large amounts of power to the implant device. However, the FIS must also be able to operate, from time to time or in the event of a battery or other failure, using an external behind-the-ear (BTE) unit, or other external unit, which requires a power transfer at much lower power levels than are needed for recharging. That is, in the FIS, during one mode of operation, a relatively large power level must be transferred for charging the implanted power storage element, e.g., a rechargeable battery. However, in another mode of operation, the implant is operated and powered from a BTE unit, or other external unit, during which mode a relatively small power level is transferred to the implant device. The ratio of these power levels may be, e.g., about 30 to 1. Unless the coil set, i.e., the external coil and implanted coil, are altered between these different load conditions, a mismatch loss on the order of 14dB may occur, which mismatch may reduce the transfer efficiency from about 70% to about 3%! The present invention advantageously eliminates such a mismatch loss.

In accordance with one aspect of the invention, a time-varying impedance transformer is utilized to make the mismatch loss constant. The control of the mismatch is determined by the load impedance, once all other components are fixed. However, because an implant device of the type with which the present invention is used may require a range of output voltages, and output currents, the effective load resistance is not equivalent to a single load resistance, but rather varies as a function of time dependent upon the required circuit operation. The time-varying impedance transformer provided in the implant device by the invention thus operates to stabilize (make constant insofar as possible) the ratio of output voltage and output current as seen by the coil set, thereby rendering the mismatch loss constant, even though the individual output voltages and output currents do vary.

In accordance with another aspect of the invention, a switching regulator circuit is employed as the time varying impedance transformer. Advantageously, a switching regulator circuit provides for the efficient transfer of electrical power from one voltage level to another. A switching regulator operates as a DC-to-DC impedance transformer. That is, at its input, the switching regulator consumes the required current at the source voltage level, and transforms the current to a new level at a different output voltage. Since energy is neither created nor destroyed, the switching regulator functions as a power transformer, with some loss occurring (as determined by the converter efficiency). Hence, in accordance with the present invention, a switching regulator included as part of the implant circuitry is controlled in an appropriate manner so that the resulting impedance transforming property of the switching regulator reduces mismatch loss variations.

It is thus a feature of the present invention to provide an implantable medical device, e.g., an implantable cochlear stimulator or other implantable neural stimulator, that employs a switching regulator circuit as part of the implanted circuitry. The switching regulator is controlled, as energy is inductively coupled into the implant circuitry through a coil set that includes an external coil and an implanted coil, to operate as a varying impedance transformer. More particularly, the impedance is varied so as to minimize mismatch losses as seen at the power source, thereby improving the power transfer efficiency into the implant device.

It is a further feature of the invention to provide an implantable time-varying impedance transformer wherein there are no circuit value or wiring changes needed to handle varying output load impedance. Rather, all control is entirely electronic.

One advantage of the invention is that the frequency of the carrier signal (the signal applied to the external coil) is fixed, thereby avoiding regulatory or other problems incident to using variable frequency carrier signals.

An additional advantage of the invention is that the effective DC load resistance of the implanted circuitry (output voltage divided by output current) is transformed to effect an AC circuit mismatch loss, so that the lowest insertion loss of the coil set (i.e., the highest power transfer efficiency between the external coil and implanted coil) may be utilized.

Still another advantage of the invention is that the voltage transform ratio of the coil set is, within certain practical constraints, relatively independent of the voltage at the output load.

Another advantage of the invention, when used in combination with a smart external power source that can regularly measure the impedance as seen looking into the external coil and communicate this measured impedance to the implant device, is that the impedance transforming process that occurs in the implant device, acting upon the measured impedance information obtained from the smart external device, may also be used to compensate for variations in transfer efficiency that occur due to coil separation.

BRIEF DESCRIPTION OF THE DRAWINGS

The above and other aspects, features and advantages of the present invention will be more apparent from the following more particular description thereof, presented in conjunction with the following drawings and appendix wherein.

Figure 1:
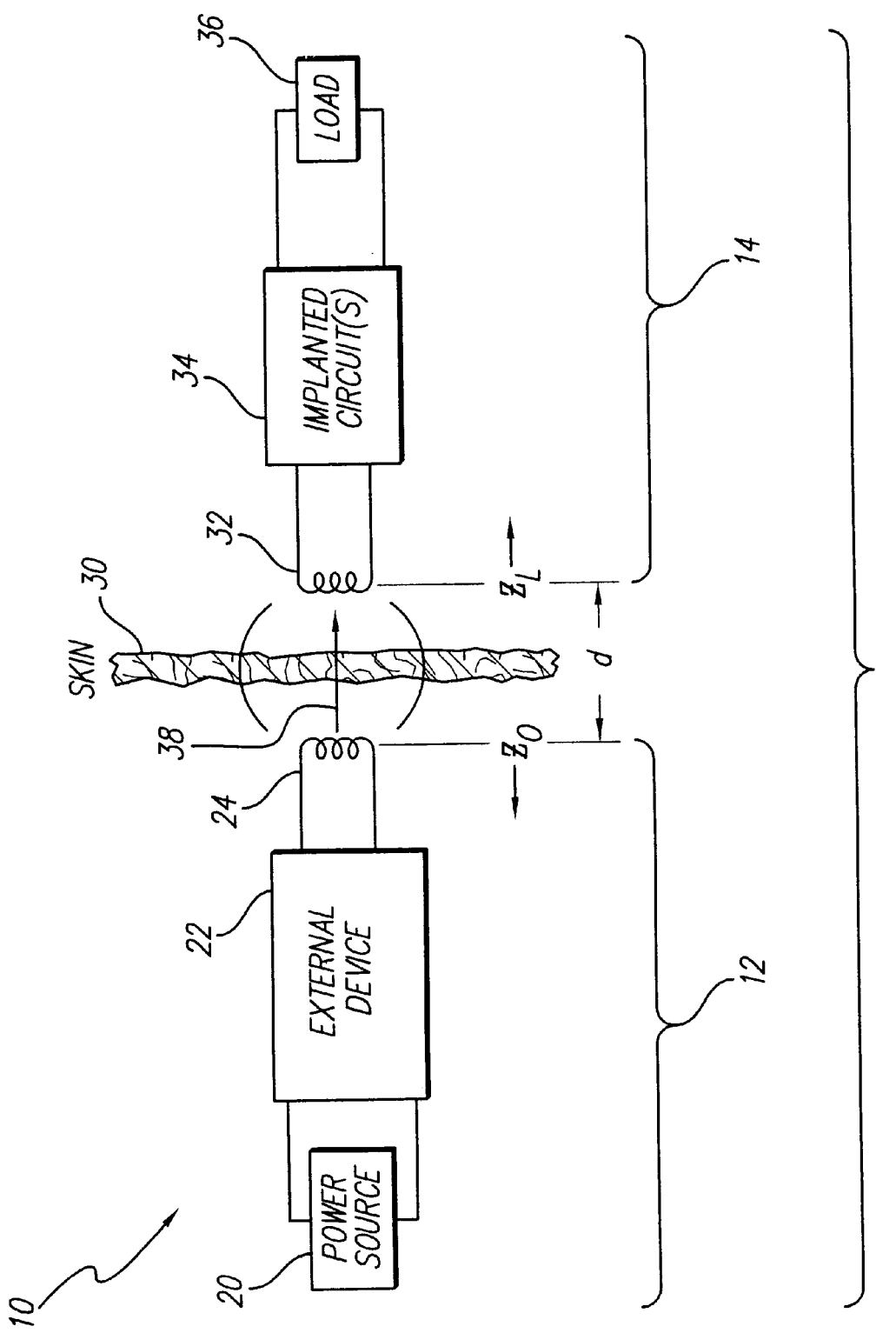
FIG. 1 is block diagram illustrating the use of an external device to inductively couple power into an implant device.

Appendix A is a copy of the article entitled "Source resistance: the efficiency killer in DC-DC converter circuits", previously referenced.

Corresponding reference characters indicate corresponding components throughout the several views of the drawings. The present invention addresses the above and other needs by

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Turning first to FIG. 1, there is shown a block diagram of a power transfer system 10 that includes an external power transfer system 12 and an implanted device 14. The external power transfer system 12, also referred to as the external system 12, includes a power source 20, an external device or circuit 22, and an external coil 24. As used herein, the word "external" means not-implanted, e.g., on the outside of the skin 30, of a patient or user.

The implanted device 14, as seen in FIG. 1, includes an implanted coil 32, an implanted circuit(s) 34, and a load 36. As used herein, the term "implanted" means implantable subcutaneously, i.e., placed under the skin 30 of the user or patient. For some embodiments of the invention, it is contemplated that the power transfer system 12 may itself be implanted, wholly or partially, the invention for such embodiment thus being directed to the transmission of power between two implantable devices.

For purposes of the present invention, the function performed by the implanted or implantable device 14 is not important. The implant device 14 may perform any desired function, e.g., tissue stimulation, sensing and monitoring physiological parameters, injecting medication into the blood or tissue of the patient, and the like. A preferred application for the invention is for use with an implantable cochlear stimulator (ICS), which ICS provides stimulation to the auditory nerve fibers in the cochlea of the patient as a function of sounds sensed external to the patient. A representative ICS system is illustrated in U.S. Pat. No. 5,603,726, incorporated herein by reference.

Regardless of the type of function performed by the implant device 14, it must receive operating power from the external system 12. Typically, power is transferred into the implant device 14 via inductive coupling. That is, an ac power signal, generated by the external device 12 is applied to the external coil 24. This ac power signal induces a corresponding ac power signal in the implanted coil 32 whenever the external coil 24 and the implant coil 32 are sufficiently close to each other so as to permit the alternating magnetic field created by passage of the ac power signal in the external coil 24 to pass through the implanted coil 32. Such magnetic coupling of two coils is commonly referred to as inductive coupling.

The power coupled from the external coil 24 to the implanted coil 32 is represented in FIG. 1 by the straight arrow 38. The magnitude of the coupled power 38 is predominately a function of the distance between the two coils 24 and 32 as well as the impedance match between the implant device 14 and the external device 12.

The distance between the two coils 24 and 32 is referred to herein as the "implant distance", and is represented in FIG. 1 as the distance "d".

The input impedance of the implanted device 14 is represented in FIG. 1 by the symbol $Z_L$. The value of $Z_L$ is determined in large part by the value of the load 36 attached to the implanted device 34, as well as the components used to make the implanted circuit(s) 34. The value of the load 36 varies significantly from patient to patient, and over time for the same patient, depending upon the operation of the implanted device 34. Thus, the input impedance $Z_L$ of the implant device 14 is not a constant, as has often been assumed in the past, but is a variable that may vary over time and from patient to patient by as much as a factor of 30 or more.

The output impedance of the external system 12 is represented in FIG. 1 by the symbol $Z_0$. The value of $Z_0$ is determined in large part by the circuit components from which the external device 22 is made.

It is an object of the present invention to provide, as part of the implanted circuits 34, an impedance transformer that automatically adjusts the input impedance $Z_L$ of the implanted system 14 so as to provide the lowest power insertion loss of the coil set. Here, the "coil set" refers to the external coil 24 and the implanted coil 32. The power transfer through the coil set follows the well known relationships of the "double-tuned" network that has been used in radio circuits since its earliest times. In a weakly coupled coil set (coupling coefficient less than 0.2), the wires of the coils contribute to the losses of the power transfer. The parameters that effect the power transfer are: coil geometry (diameters and spacings), operating frequency, numbers of turns in the coils, coil resistance, and source and load resistance. Generally, the coils are of different diameters, and have different numbers of turns. The impedance levels $Z_0$ and $Z_L$, using the relationships of the double-tuned network are therefore generally different. However, for any given coil set, operated at a given spacing and frequency, there is an optimum $Z_0$ and $Z_L$ that provide the lowest insertion loss. These values may be calculated from the parameters listed above. Under such minimum insertion loss condition, a maximum amount of power 38 may advantageously be coupled into the implant device.

Figure 2:
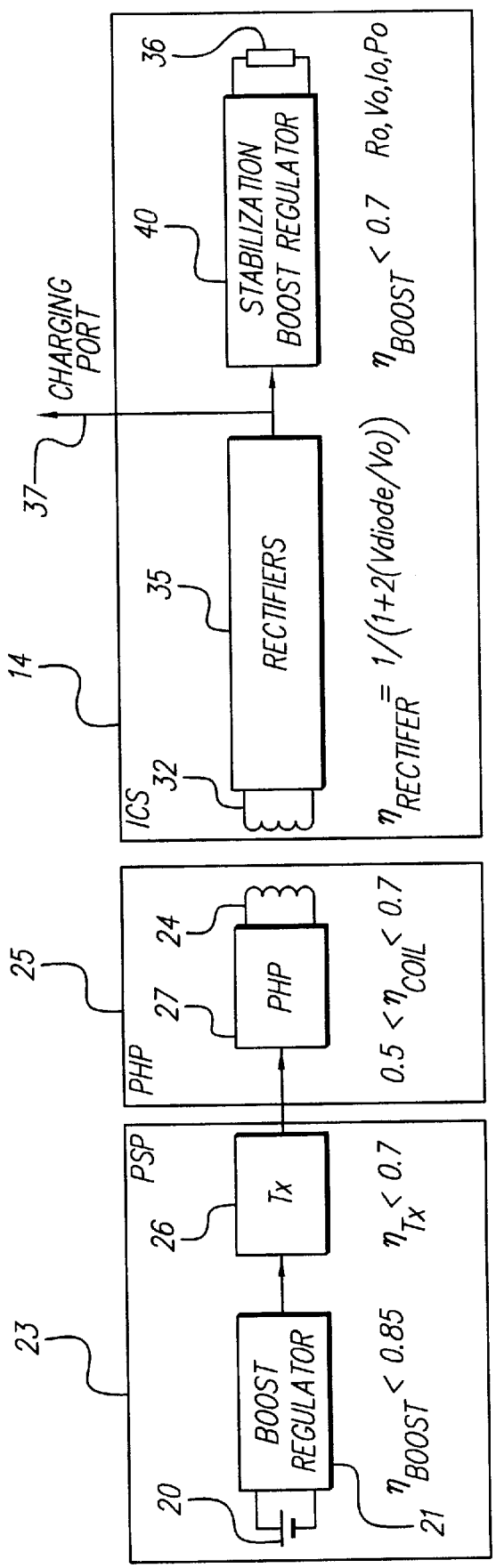
FIG. 2 is a block diagram illustrating the use of a stabilization boost regulator as part of the implanted circuits in accordance with the present invention.

Turning next to FIG. 2, there is shown a block diagram illustrating the use of a stabilization boost regulator 40 as part of an implanted device 14 in accordance with the present invention. The implanted device 14 shown in FIG. 2 comprises an implantable cochlear stimulator (ICS), although this is only exemplary. The implanted device 14 includes an implanted coil 32, as described in FIG. 1. The implanted coil 32 interfaces with an external pocket head piece (PHP) 25, driven by an external pocket speech processor (PSP) 23.

The PSP 23 includes a power source 20, e.g., a battery, that provides operating power to a boost regulator circuit 21. The boost regulator circuit 21, in turn, provides operating power to a suitable transmitter circuit 26, Tx, that drives the PHP circuitry 27 and external coil 24, with a suitable modulated ac signal that is coupled into the ICS circuitry 14 through the implanted coil 32, as described above in connection with FIG. 1.

It should be noted that there is much circuitry included in a typical PSP 23, PHP 25 and ICS 14 that is not shown in FIG. 2. Such additional circuitry relates to how audible signals are sensed and converted to appropriate control signals for directing the ICS to stimulate cochlear tissue through a suitable electrode implanted in the cochlea, thereby allowing the user to experience the sensation of hearing through direct electrical stimulation of his/her auditory nerve. Such additional circuitry is not relevant to the present invention, and is therefore not disclosed. (The interested reader can refer, e.g., to U.S. Pat. Nos. 3,751,605; 4,207,441; 4,408,608; 4,428,377; 4,532,930 and 5,603,726, which patents are incorporated herein by reference, for a detailed description of the circuitry associated with and the operation of various types of cochlear implant systems.) Rather, the present invention focuses on the manner in which the implant system 14, which may be any type of implant system, e.g., a cochlear implant system, may more efficiently receive and process power received from an external source through the use of an implanted time-varying impedance transformer that monitors the load coupled to the implant device, and makes adjustments, as required, to present a more or less constant load to the external circuitry that couples power into the implant device.

Thus, in operation, as shown in FIG. 2, the ICS 14 receives operating power from the PSP 23 through the PHP 25, and more particularly through the coil set that includes the external coil 24 and the implanted coil 32. Such power, when received at the implanted coil 32 is rectified using a rectifier circuit 35. The rectified power is then available to power the ICS circuitry, including any rechargeable battery that may be included as part of the ICS, or an implanted speech processor, e.g., through a charging port 37, as well as a stabilization boost regulator circuit 40. The stabilization regulator circuit 40 provides power for the circuits of the ICS, which circuits are represented in FIG. 2 by the load 36. For an ICS, the load 36 includes, in addition to most of the signal processing circuitry that receives and processes commands from the speech processor, an electrode array that has been implanted in the cochlea of the user. It is this stabilization regular circuit 40, for the particular ICS embodiment shown in FIG. 2, that functions as a time-varying impedance transformer in accordance with the principles of the present invention.

In the implementation of the invention shown in FIG. 2, the various efficiencies, η, for each stage of the system, are represented. By way of example, the efficiency of the external boost regulator 21 is shown as being less than 0.085 ($\eta<0.85$); the efficiency of the external coil 24 is $0.5<\eta_{coil}<0.7$; the efficiency of the rectifier 35 is $\eta_{rectifier}=1/(1+2\times V_{diod}/V_O)$; and the efficiency of the stabilization boost regulator 40 is $\eta_{Boost}<0.7$. A preferred transfer efficiency through the entire system should approach 70%, although transfer efficiencies much less than 70%, e.g., 35–50%, may still represent a significant improvement over what has been achieved in the past. Proper operation of the circuitry shown in FIG. 2 maintains a proper voltage/current ratio at its input as the output load ($V_O$, $R_O$, $I_O$, $P_O$) varies.

Figure 3:
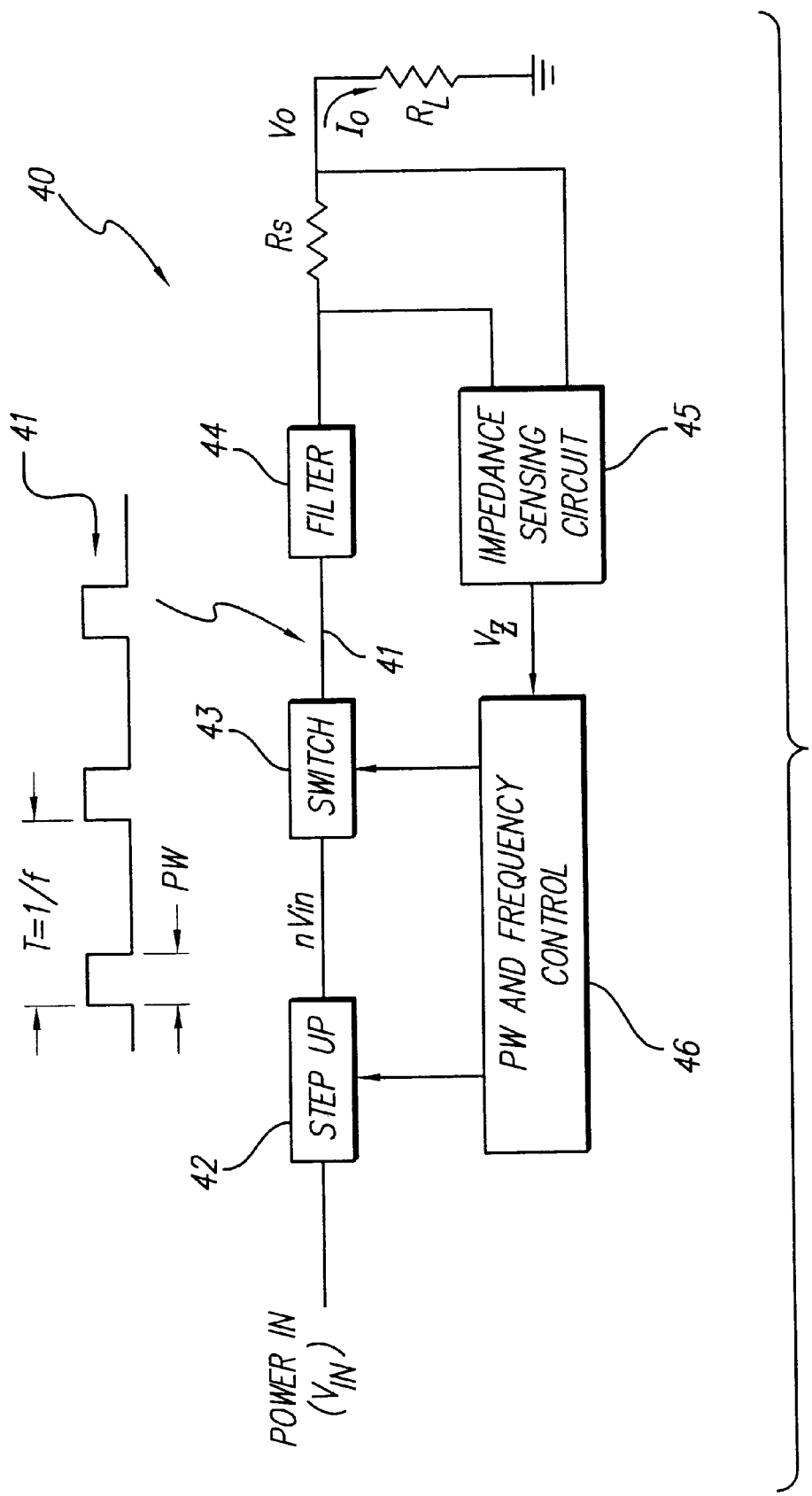
FIG. 3 shows a functional block diagram of the stabilization boost regulator shown in FIG. 2.

Turning next to FIG. 3, a functional block diagram of one embodiment of a stabilization boost regulator circuit 40 is illustrated. It is to be emphasized that the block diagram of FIG. 3, as well as the other block diagrams included in the figures, is functional in nature. Those of skill in the art, given the functional descriptions presented herein, will be able to fashion suitable circuitry, whether dedicated analog, digital, or combinations of analog/digital circuitry, and/or whether implemented using state-diagram driven, or firmware/software controlled circuits, to carry out the indicated functions.

The stabilization boost regulator circuit 40 shown in FIG. 3 functions as a switching regulator circuit. As such, it may include, but does not have to include, a step up circuit 42 that selectively multiplies, or steps up, the voltage $V_{IN}$ of the "Power In" signal by a prescribed amount, as needed in order to allow the output voltage, $V_O$, to be within a desired range. That is, the output of the step up circuit 42, when used, will typically be a voltage having a value of $nV_{IN}$, where n is an appropriate multiplication factor. Such voltage step up circuits are known in the art.

In one specific embodiment, a single-ended primary inductance converter (SEPIC) circuit was employed as the "step up circuit 42" that operated continuously between step-up and step-down at its output. In practice, any suitable switching circuit may be used, including step up, step down, or buck/boost circuits. The essential element is that the switching mechanism resemble an electronically-controlled transformer.

Following step up circuit 42, if used, is a switch 42 that switches the signal $nV_{IN}$ in accordance with a desired duty cycle. That is, the switch 42 is turned ON for a desired portion of a time period T, during which ON time the power signal is passed through the switch 43 to the next functional element in the circuit. When the switch is turned OFF, then the power signal is not allowed to pass through the switch 43. The result, at the output of the switch 43, is a pulsed waveform 41 having a series of pulses with a pulse width PW (representing the ON time of the switch 43) repeating every T seconds. The frequency, f, of the pulsed waveform is thus 1/T. The duty cycle of the waveform, expressed as a percentage, is Duty Cycle=$(PW)/(T)\times100\%$.

The duty cycle may thus vary from 0% (switch 43 OFF all the time), to 50% (switch 43 ON half of the time and OFF half of the time), to 100% (switch 43 ON all the time), or any other value between 0% and 100%. As the pulsed signal is applied to a suitable filter 44, e.g., a low pass filter, it is converted to a dc level, or output voltage $V_O$, the amplitude of which varies as a function of the duty cycle. Thus, control of the duty cycle of the switched waveform $nV_{IN}$ controls the amplitude of the output voltage $V_O$.

Still referring to FIG. 3, the output of the filter circuit 44 is coupled to the load, $R_L$, through a sensing resistor $R_s$, or equivalent current-sensing element. When a sensing resistor $R_S$ is used, it will typically be a very small value, e.g., 1 ohm or less. Such element is used to provide a measure of the output current $I_O$ that is flowing into the load $R_L$. Any suitable element that senses dc current flow, such as a dc current probe, may be used as the sensing element $R_S$.

For the embodiment shown in FIG. 3, the voltage developed across the sensing element $R_S$ provides a measure of the current $I_O$ flowing therethrough. This value of $I_O$, coupled with the output voltage $V_O$, is coupled to an impedance sensing circuit 45. The impedance sensing circuit 45 determines the output impedance based on the measured values of $I_O$ and $V_O$ (impedance, Z, is equal to $V_O/I_O$), and produces a voltage signal $V_Z$ as a function thereof. The signal $V_Z$ is then applied to a suitable pulse-width and frequency (PW and Freq.) control circuit 46 that, in turn, generates the appropriate control signals for controlling the step up circuit 42 and switch 43 so that a desired impedance transformation takes place.

Figure 4:
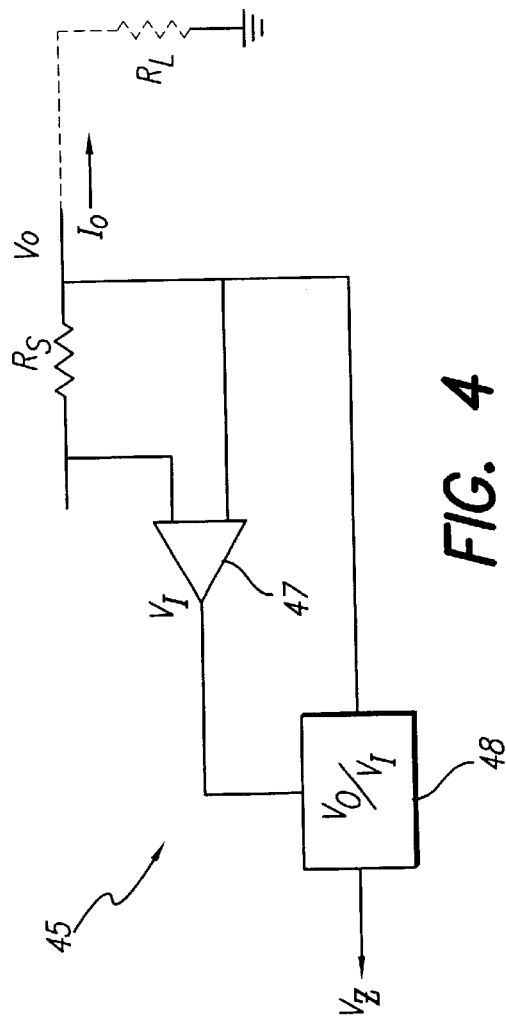
FIG. 4 illustrates a functional block diagram of the impedance sensing circuit shown in FIG. 3.

Next, with respect to FIG. 4, there is shown one embodiment of a representative functional block diagram of the impedance sensing circuit 45 shown in FIG. 3. Such impedance sensing circuit 45 includes a differential amplifier 47 that monitors the voltage across the sense resistor $R_S$ and generates an output voltage, VI, as a function thereof. The output voltage $V_O$ and the current-sense voltage $V_I$, are then applied to a division circuit 48 where the output voltage $V_O$ is divided by the current-sense voltage $V_I$, to produce the impedance voltage $V_Z$. The impedance voltage $V_Z$ is then applied to the PW and Freq. Control circuit 46 (FIG. 3) so that appropriate adjustments are made to the PW and duty cycle in order to automatically bring about needed impedance transformation whenever a significant change in the power ($V_O$ and $I_O$) delivered to the load $R_L$ is sensed. In this manner, i.e., with appropriate impedance transformations automatically occurring within the implanted device 14, the impedance seen by the external source 23 remains relatively constant, thus maintaining the efficiency with which power is coupled into the implanted device 14.

It should also be noted that the impedance transforming process made possible by the invention may also be used to compensate for variations in transfer efficiency that occur due to coil separation, i.e., the separation between the external coil 24 and the implanted coil 32.

Figure 5:
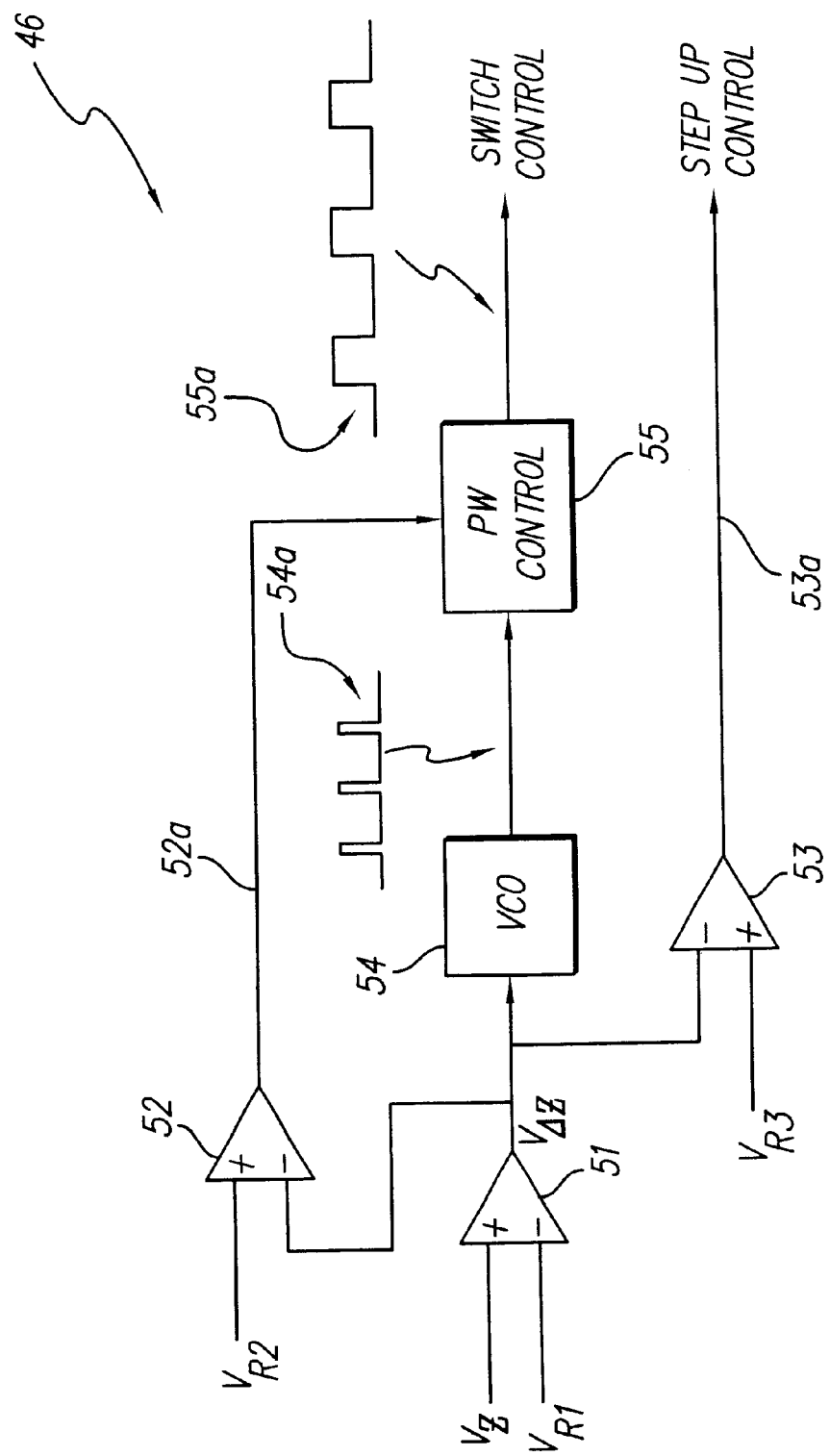
FIG. 5 depicts a simplified functional block diagram of the pulse width (PW) and frequency control circuit shown in FIG. 3.

Turning next to FIG. 5, a simplified functional block diagram of one embodiment of the pulse width (PW) and frequency control circuit 46 is shown. As seen in FIG. 5, a first differential amplifier 51 compares the impedance voltage $V_Z$ to a first reference voltage $V_{R1}$, producing an output voltage $V_{AZ}$ representative of changes in the impedance voltage compared to the first reference voltage $V_{R1}$. That is, the output voltage $V_{AZ}$ provides an indication of changes in the output impedance $Z_O=V_O/I_O$. The voltage $V_{AZ}$ drives a voltage controlled oscillator (VCO) 54. The VCO 54 generates a pulsed waveform 54a having fixed narrow pulses. This waveform 54a is applied to a pulse width (PW) control circuit 55, which converts the narrow pulse widths of the waveform 54a to a waveform 55a having wider pulse widths that vary as a function of a PW control signal 52a. The PW control signal 52a is generated by a second differential amplifier 52, or comparator circuit, that compares the output voltage $V_{AZ}$(which represents changes in output impedance) to a second reference signal $V_{R2}$, and causes the pulse width to change as a function of the difference between $V_{AZ}$ and $V_{R2}$. In this manner, changes in the output impedance signal $V_Z$ relative to a first threshold $V_{R1}$ affect the frequency of the switch control signal 55a, and changes in the signal $V_{AZ}$ relative to a second threshold $V_{R2}$ cause the pulse width (PW) of the switch control signal 55a to vary. As the pulse width and frequency of the control signal 55a vary, an impedance transformation takes place that makes the coupling of power into the implant device 14 more efficient.

In the event that the output voltage $V_O$ changes a significant amount due to large changes that occur in the power delivered to the load of the implant device, e.g., should changes be needed in the impedance transformation beyond those possible through just frequency and pulse width control, then the multiplication factor n associated with the step-up control circuit 42 (FIG. 3) is adjusted accordingly. Control of the multiplication factor n is triggered by control signal 53a, generated by a third differential amplifier 53, or comparator circuit, that compares the change in impedance voltage $V_{AZ}$ to a third reference signal $V_{R3}$.

Figure 6:
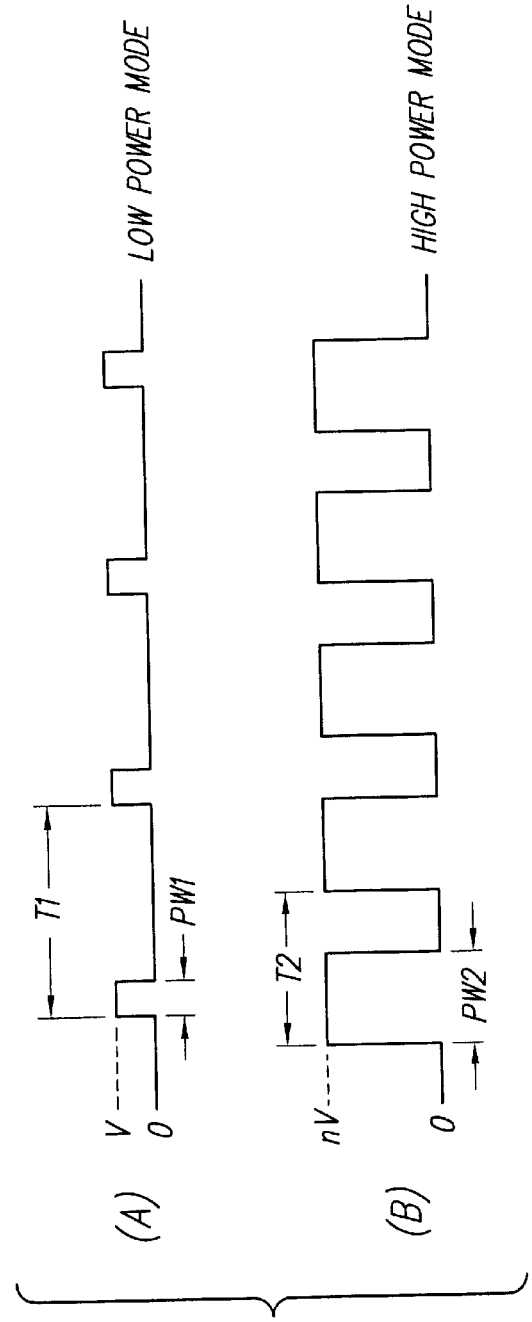
FIG. 6 is a timing diagram that illustrates the operation of the stabilization boost regulator shown in FIG. 2 for two different power modes, a low power mode and a high power mode.

Thus, under a low power operating mode, e.g., a mode where the power ($V_O$, $I_O$) delivered to the load $R_L$ is relatively low, a typical switch control signal 55a may have an amplitude V, a pulse width PW1, and a period T1 that is as shown in FIG. 6, waveform (A). In such mode, the duty cycle of the stabilization boost regulator 40 remains relatively low. Under a high power operating mode, e.g., a mode where the power ($V_O$, $I_O$) delivered to the load $R_L$ is relative high, a typical switch control signal 55a may have an amplitude nV, a pulse width PW2, and a period T2 that is as shown in FIG. 6, waveform (B). In such mode, the duty cycle of the stabilization boost regulator 40 may be relatively high. In either operating mode, however, the impedance of the implant device 14, as seen by the external charging device 12, may remain relatively constant, thereby promoting the efficient coupling of power into the implant device.

It should be noted that the changes in frequency that occur in the control signal 55a (e.g., as the period varies from T1 to T2, FIG. 6) are not related to the frequency of the rf signal that is inductively coupled form the external coil 24 to the implanted coil 32. Such rf frequency of the coupling signal may remain at a constant frequency, e.g., 49 MHz, thereby simplifying the external circuitry and minimizing regulatory requirements associated with variable frequency transmissions.

Other embodiments of the invention may also be used. Further, as those of skill in the art will recognize, the use of a switching regulator circuit may easily lead to instability problems. That is, switching regulators are prone to "bistability", as discussed in article: "Source resistance: the efficiency killer in DC-DC converter circuits", previously referenced. Such article discusses, intra alia, the common design criteria and design problems associated with DC-DC converters.

In order to avoid the bistability problems that have plagued prior art designs, an unconventional extended control loop may be employed. Such extended control loop prevents bistable runaway, and allows full operation of the circuitry (FIG. 3 et seq.) described herein. Basically, such extended control loop includes a fold-over loop, and an under-voltage loop, which in combination prevent the switching regulator from running away, and tell the RF source to increase or decrease its output level. A block diagram of this approach is shown in FIG. 7.

Figure 7:
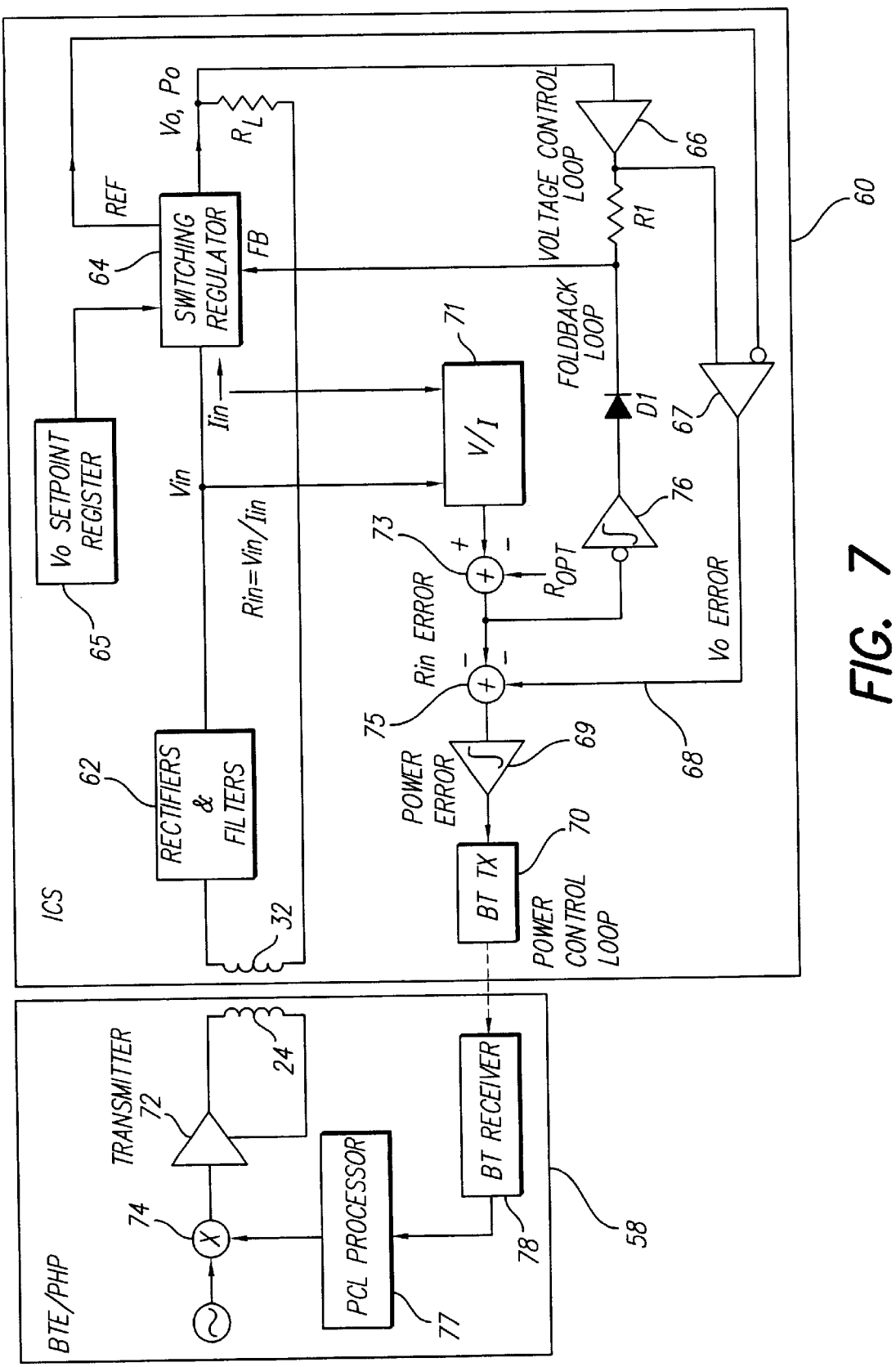
FIG. 7 illustrates an unconventional extended control loop that is used with the present invention in order to prevent bistability problems, which extended control loop includes both a fold-over loop, and an under-voltage loop.

As seen in FIG. 7, the system includes external components 58 and an implanted unit 60, e.g., an ICS. The external components are typically realized in a BTE unit coupled to a pocket head piece, or PHP, and include an RF signal source coupled to a transmitter 72 through a modulator 74. The transmitter 72 drives the external coil 24. A back telemetry (BT) receiver 75, also included in the external components 58, receives back telemetry signals from the implanted unit 60, which signals are inputted to a processor 77. The processor 77, in turn, processes the signals in an appropriate manner so as to use the information contained therein to modulate the RF power signal that is sent to the transmitter 72.

The implanted unit 60 includes the implanted coil 32. Signals received through the implanted coil 32 are rectified and filtered using the rectifier and filter circuits 62 to create an input voltage $V_{IN}$. The input voltage $V_{IN}$, as well as an input current, $I_{IN}$, are applied to a switching regulator 64. An output voltage ($V_O$) setpoint register 65 provides a reference voltage, or signal, to the switching regulator 64 that defines the desired output voltage, $V_O$. The switching regulator thus generates the output voltage $V_O$ at a certain power level, $P_O$, into the ICS load $R_L$.

A voltage control loop, comprising a buffer amplifier driving a resistor R1 provides a feedback (FB) signal to the switching regulator. A difference amplifier 67 compares a reference voltage from the switching regulator 64 with the buffered output voltage (output of buffered amplifier 66) to generate an error voltage, $V_O$ Error, on signal line 68. This signal is compared with an Rin Error signal, generated as discussed below, and then integrated through the use of an integration circuit 69 to create a Power Error signal. The Power Error signal is applied to a back telemetry transmitter circuit (BT TX) 70, from where it is transmitted to the back telemetry receiver 75 in the external BTE/PHP unit 58. The external unit 58 uses the received Power Error signal to adjust the level of the input power transmitted to the ICS.

The $V_{IN}$ and $I_{IN}$ signals that are applied to the switching regulator 64 are also applied to a voltage/current divider circuit 71. The ratio of the $V_{IN}$ and $I_{IN}$ signals (i.e., the input voltage $V_{IN}$ divided by the input current $I_{IN}$) provides a measure of the input impedance, or input resistance, $R_{IN}$, of the implanted ICS unit 60. Such measure of input resistance $R_{IN}$ is compared with an optimum resistance $R_{OPT}$ by a summer circuit 73, which summer circuit 73 subtracts $R_{OPT}$ from $R_{IN}$ to arrive at an $R_{IN}$ Error signal. As indicated above, the $R_{IN}$ Error signal is compared with the $V_O$ Error signal, in a summer circuit 75, to create the Power Error signal that is sent by back telemetry to the external BTE unit 58.

As further shown in FIG. 7, the $R_{IN}$ Error signal is integrated, by integrator circuit 76 and then applied through diode D1 to the feedback (FB) signal applied to the switching regulator. The output voltage $V_O$ portion of the FB signal is derived from a voltage control loop made up of the buffer amplifier 66 and resistor R1. The integrated $R_{IN}$ Error signal portion of the FB signal is derived from a foldback loop made up of the V/I divider circuit 71, the summer 73, the integrator circuit 76 and the diode D1. Advantageously, use of a voltage control loop and a foldback loop as shown in FIG. 7 may be used to avoid bistability problems in the operation of the switching regulator circuit, when needed.

From the above, it is thus seen that the present invention provides an implantable medical device, e.g., an implantable cochlear stimulator or other implantable neural stimulator, that employs a switching regulator circuit as part of the implanted circuitry. Advantageously, the switching regulator is controlled, as energy is inductively coupled into the implant circuitry through a coil set that includes an external coil and an implanted coil, to operate as a varying impedance transformer. More particularly, the impedance is varied so as to make mismatch losses as seen at the power source appear substantially constant. In turn, a constant mismatch loss allows an optimum power transfer efficiency (minimum power insertion loss) to occur.

It is further seen that the invention provides an implantable time-varying impedance transformer wherein there are no circuit value or wiring changes needed to handle varying output load impedance. Rather, all control is entirely electronic and preferably automatic.

It is also seen that the invention may operate using a carrier signal (the signal applied to the external coil) having a fixed frequency, thereby avoiding regulatory or other problems incident to using variable frequency carrier signals.

It is additionally seen that an advantage of the invention is that the effective DC load resistance of the implanted circuitry (output voltage divided by output current) is transformed to effect an AC circuit mismatch loss, so that the lowest insertion loss of the coil set (i.e., the highest power transfer efficiency between the external coil and implanted coil) may be utilized.

While the invention herein disclosed has been described by means of specific embodiments and applications thereof, numerous modifications and variations could be made thereto by those skilled in the art without departing from the scope of the invention set forth in the claims.

What is claimed is:

1. An implantable medical device adapted to receive power through an inductive link, said implantable medical device comprising:

an implantable coil adapted to receive an inductively coupled signal from a power source;

a rectifier circuit connected to the implantable coil, wherein the rectifier circuit rectifies the inductively coupled signal and produces an operating dc voltage therefrom;

electronic circuitry powered from said operating dc voltage that performs a specified function, said electronic circuitry requiring differing amounts of power as a function of how the electronic circuitry is configured; and impedance transforming circuitry connected to the rectifier circuit that monitors changes in the amount of power used by the electronic circuitry and effectuates changes in load impedance as seen by the rectifier circuit so that the load impedance as seen by the rectifier circuit remains approximately constant.

2. The implantable medical device of claim 1 wherein the impedance transforming circuitry comprises a switching regular circuit.

3. The implantable medical device of claim 2 wherein the switching regulator circuit comprises a stabilization regulator circuit selected from the group comprising: a step up, a step down, a buck/boost, and a SEPIC regulator circuit.

4. The implantable medical device of claim 3 wherein the stabilization regulator circuit includes a voltage control loop and an input resistance $R_{IN}$ error foldback loop.

5. The implantable medical device of claim 3 wherein the stabilization regulator circuit comprises:

a switch that switches the operating dc voltage generated by the rectifier circuit ON or OFF as controlled by a switch control signal, the switch control signal having a duty cycle;

a filter circuit that filters the switched operating dc voltage to produce an output voltage ($V_0$) having an amplitude that varies as a function of the duty cycle of the switch control signal;

an impedance sensing circuit that senses the output voltage ($V_0$) and output current $I_0$ delivered to the electronic circuitry; and a control circuit that generates the switch control signal as a function of changes sensed in the output voltage $V_0$ and output current $I_0$ delivered to the electronic circuitry.

6. A time-varying impedance transformer for use within an implantable medical device, said implantable medical device being coupled to an external device for receiving power through an inductive link that includes an external coil and an implanted coil, wherein the external coil and the implanted coil comprise a coil set, and wherein the amount of power coupled to the implantable medical device is a function of how much mismatch loss occurs as power is coupled into the implantable medical device, said time-varying impedance transformer comprising a switching regulator that includes means for making the mismatch loss through the coil set constant.

7. The time-varying impedance transformer of claim 6 wherein the means for making the mismatch loss through the coil set constant includes means for operating the switching regulator so as to make the ratio of output voltage and output current as seen by the coil set constant, thereby rendering the mismatch loss constant, even though individual output voltages and output currents are not constant.

8. An implantable device adapted to receive power through an inductive link, said implantable device comprising:

implantable coil means for receiving an inductively coupled signal from a power source;

rectifying means connected to the implantable coil for rectifying the inductively coupled signal and producing an operating dc voltage therefrom;

electronic circuit means powered by said operating dc voltage for performing a plurality of specified functions, wherein differing amounts of power are required by said electronic circuit means depending upon the function being performed; and impedance transforming means connected to the rectifying means for monitoring changes in the amount of power used by the electronic circuit means and effectuating changes in load impedance as seen by the rectifying means so that load impedance as seen by the rectifying means remains approximately constant.

9. The implantable device of claim 8 wherein the impedance transforming means comprises a stabilized switching regulator circuit having a voltage control loop and an input resistance $R_{IN}$ error foldback loop.

10. The implantable device of claim 9 wherein the stabilized switching regulator circuit further comprises:

switching means for switching the operating dc voltage generated by the rectifying means ON or OFF as controlled by a switch control signal, the switch control signal having a duty cycle;

filter means for filtering the switched operating dc voltage to produce an output voltage $V_O$ having an amplitude that varies as a function of the duty cycle of the switch control signal;

impedance sensing means for sensing the output voltage $V_O$ and output current $I_O$ delivered to the electronic circuit means; and control circuit means for generating the switch control signal as a function of changes sensed in the output voltage $V_O$ and output current $I_O$ delivered to the electronic circuitry.

11. A method of receiving power within an implantable device through an inductive link, comprising:

receiving an inductively coupled signal from an external power source through the inductive link;

rectifying the inductively coupled signal and producing an operating dc voltage therefrom;

applying the operating dc voltage to a multi-function electronic circuit contained within the implantable device, wherein the power consumed by the multi-function electronic circuit varies depending upon the function being performed by the electronic circuit; and monitoring changes in the amount of power used by the electronic circuit; and effectuating changes in load impedance as seen at an input of the inductive link so that load impedance as seen by the inductive link may be kept approximately constant.

12. The method of claim 11 wherein effectuating changes in load impedance to keep load impedance approximately constant, as seen at the input of the inductive link, comprises applying a voltage control loop and an input resistance error foldback loop to a stabilized switching regulator circuit.

13. The method of claim 11 wherein monitoring changes in power and effectuating changes in load impedance comprises:

switching the operating dc voltage ON or OFF as controlled by a switch control signal, the switch control signal having a duty cycle;

filtering the switched operating dc voltage to produce an output voltage $V_O$ having an amplitude that varies as a function of the duty cycle of the switch control signal;

sensing the output voltage $V_O$ and output current $I_O$ delivered to the multi-function electronic circuit, wherein the ratio of $V_O$ to $I_O$ comprises a measure of the load impedance; and generating the switch control signal as a function of changes sensed in the output voltage $V_O$ and output current $I_O$ delivered to the multi-function electronic circuitry.

* * * * *